United States Patent [19]

Weisrock

[11] 4,301,247
[45] Nov. 17, 1981

[54] METHOD FOR IMPROVING XANTHAN YIELD

[75] Inventor: William P. Weisrock, Tulsa, Okla.
[73] Assignee: Standard Oil Company (Indiana), Chicago, Ill.
[21] Appl. No.: 214,398
[22] Filed: Dec. 8, 1980
[51] Int. Cl.$^3$ .............................................. C12P 19/06
[52] U.S. Cl. ................................... 435/104; 435/244; 435/910
[58] Field of Search ............................... 435/104, 244
[56] References Cited

U.S. PATENT DOCUMENTS 3,328,262 6/1967 Lindblom et al. .............. 435/104 X
4,245,046 1/1981 Demain et al. ...................... 435/104

OTHER PUBLICATIONS

Rogovin et al. in Biotechnology and Bioengineering, vol. 12, pp. 75-83, (1970).

Primary Examiner—Lionel M. Shapiro
Attorney, Agent, or Firm—William E. Murray; Fred E. Hook

[57] ABSTRACT

In the production of xanthan gum by action of Xanthomonas bacteria on a nutrient medium, the yield of xanthan gum can be improved by the addition of deoxycholate or cholate to the nutrient medium at the time of inoculation of the bacteria on the nutrient medium.

11 Claims, No Drawings

METHOD FOR IMPROVING XANTHAN YIELD

INTRODUCTION

The present invention relates to a method for improving the efficiency of the process for production of heteropolysaccharides, such as xanthan gum, by action of bacterial of the genus Xanthomonas on suitable nutrient media. Particularly, it is concerned with improvement of the yield of xanthan gum during fermentation. More particularly, this invention relates to a method in which a compound selected from a group consisting of deoxychol acid, cholic acid, salt thereof, and mixtures thereof is added to the nutrient medium to improve the xanthan yield.

BACKGROUND OF THE INVENTION

Fermentation of inoculated medium with Xanthomonas organisms for 36 to 72 hours under aerobatic conditions results in the formation of xanthan gum which is separated from other components of the medium by precipitation with acetone or methanol in a known manner. Because of the time required to ferment each batch, the low biopolymer content of the fermented medium and the processing steps required for recovery and purification of the product, xanthan is relatively expensive. Earlier work has indicated that heteropolysaccharides produced by the action of Xanthomonas bacteria on carbohydrate media have potential application as film-forming agents, as thickeners, for body-building agents, and edible products, cosmetic preparations, pharmaceutical vehicles, oil field drilling fluids, fracturing liquid, and emulsifying, stabilizing and sizing agents. Heteropolysaccharides, particularly xanthan gum, have significant potential as mobility control agents in micellar polymer flooding. Xanthan gum has excellent viscosifying properties at low concentration. It is resistant to shear degradation and exhibits only minimal losses in viscosity as a function of temperature, pH, and ionic strength. For these reasons, it is an attractive alternative to synthetic polyacrylamides for enhanced oil recovery operations. However, in order for xanthan gum to be used in enhanced oil recovery operations as a mobility control agent, the cost must be sufficiently low to make such operations economical. It has been shown that the economics of xanthan gum fermentation are sensitive, at least in part, to the yield of xanthan produced in relationship to the amount of glucose consumed. Therefore, any process improvements which enhance xanthan yield will improve the overall economics. For example, in a normal fermentation process increasing the xanthan yield from 60% to 80% can lower the per pound price of xanthan by as much as 10%.

The most pertinent prior art of which I am aware includes the following:

1. P. Rogovin, et al., 1970, Continuous Fermentation to Produce Xanthan Biopolymer:Laboratory Investigation, Biotechnology and Bioengineering, XII, pp. 75-83.
2. G. P. Lindblom, et al., U.S. Pat. No. 3,328,262, "Heteropolysaccharide Fermentation Process".

SUMMARY OF THE INVENTION

The present invention covers a process for production of heteropolysaccharides by culturing a microorganism of the genus Xanthomonas in a nutrient medium and recovering the heteropolysaccharide containing product. The improvement covers culturing the microorganism in the presence of a sufficient amount of an additive compund selected from a group consisting of deoxycholic acid, cholic acid, salts thereof, and mixtures thereof, whereby the yield of the heteropolysaccharide produced is increased.

DETAILED EMBODIMENTS OF THE INVENTION

The present invention is further illustrated by describing the culturing techniques which can be varied by those skilled in the art. Xanthan of the present invention can be produced at higher yield either by a batch mode in a shake flask culture or in a batch fermentor, or by continuous fermentation.

In a batch method utilizing the shake flask culture, a volume of nutrient medium is charged into a culture flask, sterilized, and inoculated with an active culture of Xanthomonas species at a ratio of inoculum to medium of from about 1 to 10 to about 1 to 20. The flask is agitated to provide aeration to the culture, and the incubation temperature is controlled. The incubation is continued for about 48 to 96 hours, or until the reaction is complete.

In a batch method utilizing a fermentor, any conventional stirred tank batch reactor may be employed. The reactor may be outfitted for aseptic operation, agitation, aeration, temperature and pH control, foam control, and measurement of dissolved oxygen. The reactor is charged with a desired volume of nutrient medium and sterilized. The fermentor is seeded with an inoculum of culture at an inoculum level of between 5% and 10% of the nutrient medium volume.

The expression, "nutrient medium", as used in the present Specification and Claims is intended to mean a medium that contains, in known or unknown compositions and proportions, essential mineral salts, trace elements, glucose or an equivalent carbohydrate, a defined source of nitrogen such as $NH_yCl$ or $NH_yNO_3$ and supplemental organic growth factors. These growth factors may include vitamins with or without appropriate amino acids. In the place of the defined nitrogen source and undefined source thereof, such as used yeast extract, yeast autolysate, or distillers dried solubles (DDS) etc., may be employed.

In carrying out the batch fermentation method of the present invention, the following broad and preferred operating conditions are noted below.

| | |
|---|---|
| Agitation: | 1000 to 2000 rpm |
| Preferably: | 500 to 1000 rpm |
| Air Rate: | 0.2 to 2 vol/vol/min |
| Preferably: | 0.5 to 1 vol/vol/min |
| Temperature: | 20 to 35° C. |
| Preferably: | 25 to 30° C. |
| pH: | 5.5 to 8 |
| Preferably: | 6.4 to 7.4 |
| Dissolved Oxygen: | 10% to 90% saturation |
| Preferably: | 20% to 60% saturation |

For the continuous fermentation method, any conventional stirred tank continuous reactor may be employed. The tank should be provided for aseptic operation, agitation, aeration, temperature, and pH control, foam control, measurement of dissolved oxygen, and level control. The continuous process can be conducted in either a single-stage or two-stage continuous mode. In the single-stage continuous mode, the concentration of the biomass is set by the concentration of the limiting nutrient being fed with medium and the biomass concentration can be varied by raising or lowering the limiting nutrient concentration. The growth limiting nutrients normally employed are nitrogen, phosphorus, and magnesium. Thus, the quantity of biomass obtained will be determined by the concentration of the limiting nutrient. A portion of the residual glucose or equivalent sugar present is converted to xanthan gum, and the latter ultimately recovered from the fermentor effluent.

In a two-stage continuous mode, the ferment from a single-stage embodiment is taken to a second fermentation stage where additional glucose or equivalent sugar is introduced and converted to xanthan. In operation of the second stage, a balance of flow of the first-stage effluent and glucose solution must approximate the flow rate of the second-stage effluent.

In a continuous culture method, a nutrient medium to be employed is charged to the reactor and sterilized.

After seeding the medium with an inoculum of culture (usually 5% to 10% of the medium volume), the culture is allowed to grow in batch mode for approximately 24 to 48 hours until the desired cell concentration is reached. Continuous culture is initiated by pumping in fresh sterile medium at a desired flow rate and drawing off product at the same rate, based on an overflow level control device. The dilution rate (flow rate divided by the fermentor liquid volume) is set to be initially 75% of the maximum specified growth rate of a culture. After two cultural turnovers (a turnover is the time required to completely replace on volume of broth in the fermentation vessel, or the reciprocal of the dilution rate), the dilution rate is set at the desired level.

In carrying out the continuous process, the following broad and preferred operating conditions are noted below:

| | |
|---|---|
| Dilution Rate: | 0.01–0.14 hrs$^{-1}$ |
| Preferably: | 0.04–0.1 hrs$^{-1}$ |
| Temperature: | 20–35° C. |
| Preferably: | 25–35° C. |
| pH: | 5.5–8.5 |
| Preferably: | 6.0–7.4 |
| Air Rate: | 0.2–2 vol/vol/min |
| Preferably: | 0.5–1 vol/vol/min |
| Agitation Rate: | 200–1200 rpm |
| Preferably: | 500–800 rpm |
| Dissolved O$_2$: | 10–90% of Saturation |
| Preferably: | 20–60% of Saturation |

In both modes of operation, representative species of the Xanthomonas genus which may be used in carrying out this invention include *Xanthomonas carotae, Xanthomonas phaseoli, Xanthomonas papavericola, Xanthomonas begoniae, Xanthomonas hederae, Xanthomonas translucens, Xanthomonas vasculorum, Xanthomonas vesicatoria, Xanthomonas incanae,* and *Xanthomonas malvacearum,* as well as *Xanthomonas campestris.* Cultures of these organisms, as well as other of this genus may be obtained from the American Type Culture Collection in Rockville, Md.

During fermentation processes for xanthan gum production, organisms of the species Xanthomonas, and particular organisms such as *Xanthomonas campestris* strain NRRL B-1459 grow and consume carbohydrates such as dextrose or other sugars. This consumption is for both cell growth and gum production. A major portion of the carbohydrate consumed is either metabolized and converted into cell biomass or used directly as a building block in the xanthan gum synthesis. At the same time, a minor portion of the carbohydrate is oxidized to $CO_2$ and water to provide energy to accomplish the above syntheses.

The total amount of dextrose or equivalent carbohydrate expended in xanthan gum production can be determined and used to calculate the yield of xanthan produced in relationship to the amount of glucose consumed. This yield can be determined in two ways; the overall yield ($y_{ov}$) is the concentration of xanthan produced per unit volume of broth divided by the difference between the initial glucose concentration and the final glucose concentration. This overall yield includes glucose consumed for cell production and in oxidation, as well as that consumed for xanthan gum production.

The other type of yield may be calculated as an adjusted yield ($y_{adj}$) which takes the amount of the glucose consumed in the biomass production and calculates xanthan gum yield on the difference, i.e., the concentration of the xanthan produced per unit volume of broth divided by the initial glucose concentration less the sum of final glucose concentration and the concentration of glucose consumed in biomass production. In the adjusted yield calculation, one gram of glucose is assumed to result in 0.5 grams of cells.

In continuous as well as batch operations, the production of xanthan gum may be significantly improved by the addition of compound selected from a group consisting of dioxycholic acid, cholic acid, salts thereof, and mixtures thereof. This addition results in significant improvements in both the overall yield and the adjusted yield as well as an increase in the overall amount of xanthan produced.

The additive compound should be added in amounts sufficient to cause increased yields in both modes of operations.

Preferably, in the batch mode, the concentration of either of deoxycholate ion or cholate ion should be at least 200 ppm in the nutrient medium, but less than an amount which would be uneconomical or toxic to the microorganisms used. More preferably, the concentration should range from 400 to 1000 ppm in the nutrient medium. Most preferably, the concentration should range from 400 to 700 ppm.

Preferably in a continuous operation mode, the concentration of either deoxycholate ion or cholate ion is at least 50 ppm in the medium. More preferably, the concentration ranges from 200 to 1000 ppm. Most preferably, the concentration ranges from 300 to 500 ppm.

With respect to the batch operation mode, the time of addition has been found to be important. The addition of the additive compound should be made during the cell growing stage of the batch mode. Preferably, the addition should occur at the time of inoculation of bacteria in the nutrient medium.

The addition of deoxycholate or cholate during a continuous process may be accomplished by adding slugs to the reactor vessel or by addition to the medium which is continuously added to the reactor.

Any form of deoxycholate or cholate is useful in this invention. Preferably, forms of deoxycholic acid, cholic acid, salts, thereof, and mixture thereof, as well as various bile extracts, that is, ox bile and beef bile are useful in this invention. Due to the cost of purified deoxycholate and chloxate compounds, use of crude extracts of bile are more preferable.

The present invention may be further illustrated by the following example.

EXAMPLE 500 ml of a medium comprising mineral salts, glucose, and ammonium chloride of the composition shown in Table 1 as charged in a 2800 ml Fermbach flask.

TABLE 1

| Component | Concentration (ppm) |
|---|---|
| Glucose | 22,500 |
| $NH_4Cl$ | 224 as N |
| $KH_2PO_4$ | 772 as P |
| $Na_2HPO_4$ | 780 as P |
| $MgSO_4 \cdot 7H_2O$ | 40 as Mg |
| $CaCl_2 \cdot 2H_2O$ | 10 as Ca |
| NaCl | 10 as Na |
| Citric Acid | 500 |
| $FeCl_3 \cdot 6H_2O$ | 2 as Fe |
| $ZnSO_4 \cdot 7H_2O$ | 0.66 as Zn |
| $CuSO_4 \cdot 5H_2O$ | 0.4 as Cu |
| $MnSO_4 \cdot H_2O$ | 0.2 as Mn |
| $Na_2MoO_4 \cdot 2H_2O$ | 0.13 as Mo |
| $H_3BO_3$ | 0.066 as B |
| KI | 0.066 as I |

The media was adjusted to a pH of 7.2, sterilized, and charged with inoculum consisting of 25 ml of an 18-hour culture of *Xanthomonas campestris* strain XCP-19 (ATCC 31601) available from the America Type Culture Collection in Rockville, Md. The 18-hour culture was completed in the same medium as shown in Table 1. Various compounds, including sodium deoxycholate, were added to the media either at the time of inoculation ($T_o$) or after cell growth had been completed but before the majority of the xanthan gum had been produced ($T_{41}$). The type of compounds, concentration of the compound, and the time of addition are shown in Table 2.

TABLE 2

| Flask No. | Treatment | Conc'n (ppm) | Time of Addition |
|---|---|---|---|
| 1 | Sodium Deoxycholate | 100 | $T_o$ |
| 2 | " | 250 | $T_o$ |
| 3 | " | 500 | $T_o$ |
| 4 | " | 750 | $T_o$ |
| 5 | " | 1000 | $T_o$ |
| 6 | " | 100 | $T_{41}$ |
| 7 | " | 250 | $T_{41}$ |
| 8 | " | 500 | $T_{41}$ |
| 9 | " | 750 | $T_{41}$ |
| 10 | " | 1000 | $T_{41}$ |
| 11 | Tween 80 | 500 | $T_o$ |
| 12 | " | 500 | $T_{41}$ |
| 13 | Sodium Lauryl Sulfate | 500 | $T_o$ |
| 14 | " | 500 | $T_{41}$ |
| 15 | Linoleic Acid (K salt) | 500 | $T_o$ |
| 16 | " | 500 | $T_{41}$ |
| 17 | Sodium Taurocholate | 500 | $T_o$ |
| 18 | Control (No addition) | — | — |

The flasks were incubated at 28° C. at 300 rpm for 96 hours. After incubation, xanthan concentration, viscosity, cell concentration (dry weight) and residual glucose were determined. The results are shown in Table 3.

TABLE 3

| Flask No. | Xanthan (%) | Cell Conc'n (gm/l) | Viscosity (cp) | $Y_{ov}(\%)$ | $Y_{adj}(\%)$ |
|---|---|---|---|---|---|
| 1 | 0.77 | 2.1 | 908 | 39 | 50 |
| 2 | 0.84 | 2.3 | 1076 | 51 | 68 |
| 3 | 1.07 | 1.8 | 2066 | 68 | 88 |
| 4 | 0.99 | 1.6 | 1550 | 66 | 83 |
| 5 | 0.86 | 1.8 | 828 | 72 | 103 |
| 6 | 0.83 | 1.8 | 788 | 44 | 56 |
| 7 | 0.65 | 1.9 | 610 | 37 | 47 |
| 8 | 0.81 | 2.4 | 1134 | 42 | 55 |
| 9 | 0.99 | 2.6 | 1848 | 46 | 61 |
| 10 | 1.06 | 2.3 | 1658 | 49 | 62 |
| 11 | 0.67 | 1.8 | 582 | 53 | 69 |
| 12 | 0.61 | 2.3 | 504 | 37 | 50 |
| 13 | — | No Growth | — | — | — |
| 14 | 0.63 | 2.0 | 692 | 57 | 91 |
| 15 | 0.68 | 2.1 | 654 | 38 | 50 |
| 16 | 0.67 | 1.9 | 582 | 38 | 50 |
| 17 | 0.9 | 2.5 | 1368 | 50 | 69 |
| 18 | 0.72 | 2.2 | 872 | 45 | 62 |

As shown in Table 3, the addition of the sodium deoxycholate gave improved yields. It should be noted that the yields shown are from flash cultures and as such are in all cases substantially below what would be expected in commercial operations such as using a batch or continuous fermentor.

I claim:

1. A process for the production of heteropolysaccharide comprising culturing a microorganism of the genus Xanthomonas in a nutrient medium, said nutrient medium containing a sufficient amount of an additive compound selected from a group consisting of deoxycholic acid, cholic acid, salts thereof and mixtures thereof.

2. A continuous process for the production of heteropolysaccharide by continuously culturing a microorganism of the genus Xanthomonas and a nutrient medium being added to a fermentation zone, withdrawing a heteropolysaccharide containing effluent from said zone while continuing said process at a rate such that an essential steady-state condition is maintained, the improvement which comprises conducting said process in the presence of an additive compound selected from a group consisting of deoxycholic acid, cholic acid, salts thereof and mixtures thereof, whereby the yield of said heteropolysaccharide produced per gram of said microorganism at steady-state is increased.

3. The process of claim 2 wherein said additive compound is added simultaneously to the fermentation zone with said microorganism.

4. The process of claim 1 or 2 wherein said deoxycholate ion has a concentration of at least 100 ppm of medium.

5. The process of claim 4 wherein said concentration of deoxycholate ion is at least 250 ppm.

6. The process of claim 5 wherein said deoxycholate ion concentration ranges from about 500-1000 ppm.

7. The process of claim 1 or 2 wherein said cholate ion has a concentration of at least 100 ppm of medium.

8. The process of claim 4 wherein said concentration of cholate ion is at least 250 ppm.

9. The process of claim 5 wherein said cholate ion concentration ranges from about 500-1000 ppm.

10. The process of claim 1 or 2 wherein said additive compound is present in the form of animal bile extract.

11. The process of claim 10 wherein said animal bile extract is selected from the group consisting of ox bile extract and beef bile extract.

* * * * *